United States Patent
Pfenniger (10) Patent No.: US 10,675,436 B2
(45) Date of Patent: Jun. 9, 2020

(54) CATHETER WITH ADJUSTABLE DIAMETER

(71) Applicant: BIOTRONIK AG, Buelach (CH)

(72) Inventor: Alois Pfenniger, Biel (CH)

(73) Assignee: BIOTRONIK AG, Buelach (CH)

( * ) Notice: Subject to any disclaimer, the term of this patent is extended or adjusted under 35 U.S.C. 154(b) by 394 days.

(21) Appl. No.: 15/622,059

(22) Filed: Jun. 13, 2017

(65) Prior Publication Data

US 2018/0015252 A1 Jan. 18, 2018

(30) Foreign Application Priority Data

Jul. 15, 2016 (EP) ..................................... 16179658

(51) Int. Cl.
*A61M 25/00* (2006.01)

(52) U.S. Cl.
CPC .... *A61M 25/0023* (2013.01); *A61M 25/0012* (2013.01); *A61M 25/0026* (2013.01); *A61M 25/0074* (2013.01); *A61M 25/005* (2013.01); *A61M 25/0043* (2013.01); *A61M 2025/0024* (2013.01)

(58) Field of Classification Search
CPC .......... A61M 25/0021; A61M 25/0023; A61M 25/005; A61M 25/04; A61M 2025/0024; A61M 2025/0293
See application file for complete search history.

(56) References Cited

U.S. PATENT DOCUMENTS

| | | | |
|---|---|---|---|
| 6,358,238 B1* | 3/2002 | Sherry | A61M 25/0023 604/524 |
| 2004/0019322 A1 | 1/2004 | Hoffmann | |
| 2007/0083132 A1* | 4/2007 | Sharrow | A61M 25/0012 600/585 |
| 2011/0166637 A1* | 7/2011 | Irwin | A61F 2/88 623/1.13 |

FOREIGN PATENT DOCUMENTS

| | | |
|---|---|---|
| EP | 0386921 A2 | 9/1990 |
| EP | 2266655 A1 | 12/2010 |
| WO | 1999016499 A1 | 4/1999 |

OTHER PUBLICATIONS

Amaro, Henrique, et al., "European Search Report", European Patent Application No. 16179658, dated Jan. 13, 2017, 5 pages.

* cited by examiner

*Primary Examiner* — Kami A Bosworth
(74) *Attorney, Agent, or Firm* — Greer, Burns & Crain, Ltd; Steven P. Fallon (57) ABSTRACT

An adjustable diameter catheter includes a wall extending in an axial direction surrounding a lumen of the catheter, the wall having at least one outer spring and at least one inner spring arranged coaxially to the outer spring. The at least one outer spring surrounds the at least one inner spring. The at least one inner and outer springs each have a distal end which are connected to one another. The at least one inner and outer springs each have a plurality of windings. A (Continued)

winding direction of the at least one outer spring is opposite to a winding direction of the at least one inner spring.

15 Claims, 10 Drawing Sheets

CATHETER WITH ADJUSTABLE DIAMETER

PRIORITY CLAIM

This application claims priority under 35 U.S.C. § 119 and all applicable statutes and treaties from prior European Application EP 16179658.6, filed Jul. 15, 2016.

FIELD OF THE INVENTION

A field of the invention catheters used for introduction of medical implants. A catheter of the invention includes an adjustable diameter.

BACKGROUND

In the field of medicine, implants are often used, which are introduced into a human and/or animal body either permanently or at least for a relatively long period of time in order to carry out replacement functions. For example, these implants are heart implants, vascular prostheses, stents or other implants, which are accurately positioned and are released in a defined manner at the site of use using catheters.

SUMMARY OF THE INVENTION

The invention concerns a catheter which allows a simple adjustment of the diameter of the lumen of the catheter, in particular in such a way that the catheter continues to be flexible and is also capable of absorbing axial forces or of withstanding axial forces. A preferred embodiment is an adjustable diameter catheter that includes a wall extending in an axial direction surrounding a lumen of the catheter, the wall having at least one outer spring and at least one inner spring arranged coaxially to the at least one outer spring. The at least one outer spring surrounds the at least one inner spring. The at least one inner and outer springs each have a distal end which are connected to one another. The at least one inner and outer springs each have a plurality of windings. A winding direction of the at least one outer spring is opposite to a winding direction of the at least one inner spring.

BRIEF DESCRIPTION OF THE DRAWINGS

Further features and advantages of the invention will be explained in the description of the drawings of exemplary embodiments of the invention given with reference to said drawings, in which.

DETAILED DESCRIPTION OF THE PREFERRED EMBODIMENTS

Preferred embodiments provide a catheter having a (preferably cylindrical) wall extended in an axial direction, which wall surrounds a lumen of the catheter, which extends in the axial direction and has, perpendicularly to the axial direction, an adjustable diameter, wherein, the diameter is the inner diameter of the lumen perpendicular to the axial direction. The wall has at least one outer spring and at least one inner spring arranged coaxially to the outer spring, wherein the outer spring surrounds the inner spring, wherein the two springs each have a distal end, wherein the two distal ends are connected to one another, and wherein the two springs each have a multiplicity of windings, which in particular are wound around the axial direction (the axial direction corresponds to the central axis of the relevant spring), and the winding direction of the outer spring is opposite the winding direction of the inner spring.

The invention thus allows the insertion of the catheter into a bodily lumen of a patient, and then the diameter of a portion of the catheter already inserted into the bodily lumen can be modified. The bending capability of the catheter is also advantageously retained and can also advantageously be influenced or adjusted by appropriate design of the springs.

Within the scope of the present invention, the distal end means that a distal end of this type, along the catheter or along the axial direction, is further removed from an operator of the catheter or a handling region of the catheter than a proximal end disposed closer to the operator or handling region. The catheter can be manually guided and operated via the handling region. The handling region can comprise a handle and in particular one or more actuation elements for operating individual functions of the catheter and is preferably provided at a (proximal) end portion of the catheter.

In accordance with a preferred embodiment of the catheter according to the invention, provision is made for the two springs to each have a proximal end opposite the respective distal end, wherein the diameter is adjustable by application of a first torque to the proximal end of the at least one outer spring and by application of a second torque to the proximal end of the at least one inner spring, wherein the first torque is opposite the second torque.

Depending on the direction of the two torques, the diameter of the individual windings of the inner and outer spring and therefore the diameter of the lumen of the wall is modified here. The two springs thus form, to a certain extent, a supporting structure of variable diameter of the wall. The spring structure formed in this way can be coated with inner and outer material layers, which will be described further below.

Provision is also made in accordance with a preferred embodiment of the catheter according to the invention for the at least one outer spring to be formed as a coil spring, in particular as a tension spring, in which adjacent windings bear against one another in the axial direction. Alternatively, the at least one outer spring can be formed as a helical spring having a multiplicity of windings which are flat in cross-section (here, the axial direction or the central axis of the spring in question lies in the considered cross-sectional plane), wherein adjacent windings of the helical spring overlap one another in the radial and axial direction.

Tension springs of this type are characterised in particular in that, with a given diameter of the tension spring, it is not possible to compress the tension spring in the axial direction, since adjacent windings bear against one another in this direction, and also in that, when the two ends of the tension spring are fixedly held, it is not possible to enlarge the diameter of the tension spring by a pressure exerted from the inside, and also in that adjacent windings can slide relative to one another in the radial direction.

Furthermore, an aforementioned helical spring is characterised in particular in that, with a limitation to a diameter smaller than the diameter of the rest configuration of the helical spring, the spring tends to draw both ends of the helical spring toward one another and to push the windings radially outwardly, and also in that it cannot support any forces in the axial direction, since the windings overlap one another and therefore can slide relative to one another in the axial direction, and also in that a sliding of the windings relative to one another in the radial direction is prevented on account of the overlap of the windings.

A particularly advantageous springs structure is therefore obtained in accordance with one embodiment when the at least one outer spring is configured as a coil or tension spring and the at least one inner spring is configured as a helical spring, because a combined spring structure of this type can absorb or withstand forces in an axial direction and can also prevent the windings from sliding against one another in a radial direction.

Furthermore, provision is made in accordance with a preferred embodiment of the catheter according to the invention for the at least one inner spring to be formed as a coil spring, in particular as a tension spring, in which adjacent windings bear against one another in the axial direction. Alternatively, the at least one inner spring can be formed as a helical spring having a plurality of windings which are flat in cross-section, wherein adjacent windings of the helical spring overlap one another in the radial and axial direction.

Furthermore, provision is made in accordance with a preferred embodiment of the catheter according to the invention for the at least one inner and the at least one outer spring to be formed together from a single continuous material layer, wherein the two interconnected distal ends are interconnected in one piece and are formed by a middle portion of the material layer.

For example, for the case in which the at least one outer and the at least one inner spring are formed as helical or tension springs, the two springs can thus be wound or formed together from a single elongated element, in particular in the form of a wire, wherein the two distal ends are then integrally interconnected and are formed by a middle portion of the elongated element or wire.

Furthermore, for example for the case in which the at least one outer spring and the at least one inner spring are formed as helical springs, provision can be made for the two springs to be wound or formed together from a material layer in the form of a flat or planar element, wherein the two interconnected distal ends are interconnected in one piece and are formed by a middle portion of the planar element.

Furthermore, provision is made in accordance with a preferred embodiment of the catheter according to the invention for the wall, for adjustment of the diameter, to have a multiplicity of outer springs and a corresponding multiplicity of inner springs arranged coaxially to the outer springs, wherein the outer springs surround the inner springs, and wherein the springs each have a distal end, wherein each distal end of an outer spring is connected to a distal end of an associated inner spring, and wherein the springs each have a multiplicity of windings, wherein the winding direction of the outer springs is opposite the winding direction of the inner springs.

Furthermore, provision is preferably made here for the springs to each have a proximal end opposite the respective distal end, wherein the diameter can be adjusted by application of a first torque to the proximal ends of the outer springs and by application of a second torque to the proximal ends of the inner springs, wherein the first and the second torque are opposite one another. Here as well, the plurality of springs form a supporting structure of the wall of variable diameter, since the diameter of the windings of the springs is enlarged or reduced depending on the direction of the torques.

With a plurality of proximal ends of inner springs, these proximal ends can be interconnected. The proximal ends of the outer springs can be interconnected in the same way, wherein a means can be provided which holds the combined or connected proximal ends and also makes it possible to exert a torque onto the proximal ends of the inner springs and onto the proximal ends of the outer springs, wherein the two torques are directed opposite one another, so as to be able to adjust the diameter of the lumen of the catheter in the previously described way.

Furthermore, provision is made in accordance with a preferred embodiment of the catheter according to the invention for the outer springs to each be formed as coil springs and to be arranged such that they form a multi-thread outer coil spring, wherein this coil spring in particular is a tension spring in which adjacent windings bear against one another in the axial direction. Alternatively, the outer springs can each be formed as a helical spring having a multiplicity of windings which are flat in cross-section, wherein in particular the helical springs are arranged such that they form a multi-thread outer helical spring, wherein adjacent windings of the outer helical spring overlap one another in the radial and axial direction.

Furthermore, provision is made in accordance with a preferred embodiment of the catheter according to the invention for the inner springs to each be formed as coil springs and to be arranged such that they form a multi-thread inner coil spring, wherein this coil spring in particular is a tension spring in which adjacent windings bear against one another in the axial direction. Alternatively, the inner springs can each be formed as a helical spring having a multiplicity of windings which are flat in cross-section, wherein in particular the helical springs are arranged such that they form a multi-thread inner helical spring, wherein adjacent windings of the inner helical spring overlap one another in the radial and axial direction.

Furthermore, provision is made in accordance with a preferred embodiment of the catheter according to the invention for the respective outer spring and the inner spring associated with the respective outer spring to each be formed from a single continuous material layer, wherein the two interconnected distal ends of the respective outer spring and of the inner spring associated with the respective outer spring are interconnected in one piece and are formed by a middle portion of the respective material layer.

A particularly advantageous spring structure is attained when the outer springs are configured as multi-thread screws or tension springs and the inner springs are each helical springs, which in turn form a multi-thread inner helical spring. Here, specifically, the advantages of the coil or tension springs can be combined with the advantages of the helical springs, because a combined spring structure of this type can absorb or can withstand forces in the axial direction and can also prevent the windings from sliding against one another in the radial direction.

For the case in which both the outer and the inner springs are formed as the helical springs, the respective outer spring and the inner spring associated with the respective outer spring can each be wound or formed from a single flat planar element, wherein the two interconnected distal ends of the respective outer spring and of the inner spring associated with the respective outer spring are interconnected in one piece and are formed by a middle portion of the respective planar element.

Furthermore, provision is made in accordance with a preferred embodiment of the catheter according to the invention for the respective material layer or the respective planar element, in order to form a pair consisting of an outer spring and an inner spring, to have a multiplicity of through-openings, in particular in the form of parallel slots. The elastic properties of the respective material layer or of the springs to be produced can thus be selectively influenced.

Furthermore, provision can be made in accordance with one embodiment of the catheter according to the invention for the inner spring or the inner springs and/or the outer spring or the outer springs to each be coated with a suitable material (for example PTFE) and/or to be provided with a lubricant (for example silicone oil) in order to reduce friction.

Furthermore, provision is made in accordance with a preferred embodiment of the catheter according to the invention for the wall of the catheter to have an elastic inner material layer facing toward the lumen of the catheter, the material layer being composed in particular of a polymer (for example Pebax) and forming and inner side of the wall facing toward the lumen. The wall can also have an elastic outer material layer, in particular composed of a polymer (for example Pebax), which forms an outer side of the wall facing away from the lumen. Here, provision is preferably made for the totality of the inner and outer springs or spring structure formed from these elements to be arranged between the two material layers and thus embedded in the wall.

As a result of these material layers of the wall, it is advantageously ensured that on the one hand the catheter can slide well in the respective bodily lumen and on the other hand components guided in the lumen itself are exposed to a minimal friction with the wall.

A further aspect of the present invention relates to a method for producing a catheter with adjustable diameter. Here, a spring structure having at least one outer spring having a multiplicity of windings and at least one inner spring having a multiplicity of windings is provided, in such a way that the at least one inner spring is arranged coaxially to the least one outer spring, the winding direction of the at least one outer spring is opposite the winding direction of the at least one inner spring, and the distal ends of the two springs are interconnected, and wherein the spring structure is preferably embedded in a wall of the catheter.

In accordance with a preferred embodiment of the method according to the invention, provision is made for the at least one outer spring to be formed as a coil spring, in particular as a tension spring, so that adjacent windings bear against one another in the axial direction. Alternatively, provision is preferably made for the at least one outer spring to be formed as a helical spring having a multiplicity of windings which are flat in cross-section so that adjacent windings of the helical spring overlap one another in the radial and axial direction.

Furthermore, provision is made in accordance with a preferred embodiment of the method according to the invention for the at least one inner spring to be formed as a coil spring, in particular as a tension spring, so that adjacent windings bear against one another in the axial direction. Alternatively, provision is preferably made for the at least one inner spring to be formed as a helical spring having a multiplicity of windings which are flat in cross-section so that adjacent windings of the helical spring overlap one another in the radial and axial direction.

Provision is particularly preferably made in accordance with one embodiment of the method according to the invention for the at least one inner and the at least one outer spring to be formed together from a single continuous material layer, wherein the two interconnected distal ends are interconnected in one piece and are formed by a middle portion of the material layer.

For the case in which the at least one outer spring and the at least one inner spring are coil or tension springs, the two springs can be wound for example from a material layer in the form of an elongated element, in particular in the form of a wire, so that the two springs each obtain a distal end, wherein the two distal ends are interconnected in one piece and are formed by a middle portion of the elongated element.

For the case in which the at least one outer spring and the at least one inner spring are each formed as a helical spring having a multiplicity of windings which are flat in cross-section, the two springs can for example be wound or formed together from a material layer in the form of a planar element so that the two springs each obtain a distal end, wherein the two distal ends are interconnected in one piece and are formed by a middle portion of the planar element.

Furthermore, provision is made in accordance with one embodiment of the method according to the invention for a spring structure having a multiplicity of outer springs each with a multiplicity of windings and having a corresponding multiplicity of inner springs each with a multiplicity of windings to be provided, in such a way that the inner springs are arranged coaxially to the outer springs, the winding direction of the outer springs is opposite the winding direction of the inner springs, and a distal end of each outer spring is connected to a distal end of an associated inner spring, and wherein the spring structure is again embedded preferably in the wall of the catheter.

Provision is made in accordance with a preferred embodiment of the method according to the invention for the outer springs to each be formed as coil springs and arranged such that they form a multi-thread outer coil spring, wherein this coil spring is in particular a tension spring, in which adjacent windings bear against one another in the axial direction.

Alternatively, provision is preferably made for the outer springs to each be formed as a helical spring having a multiplicity of windings which are flat in cross-section, wherein in particular the helical springs are arranged such that they form a multi-thread outer helical spring, in such a way that adjacent windings of the outer helical spring overlap one another in the radial and axial direction.

Furthermore, provision is made in accordance with a preferred embodiment of the method according to the invention for the inner springs to each be formed as coil springs and to be arranged such that they form a multi-thread inner coil spring, wherein this coil spring is in particular a tension spring, in which adjacent windings bear against one another in the axial direction. Alternatively, provision is preferably made for the inner springs to each be formed as a helical spring having a multiplicity of windings which are flat in cross-section, wherein in particular the helical springs are arranged such that they form a multi-thread inner helical spring, in such a way that adjacent windings of the inner helical spring overlap one another in the radial and axial direction.

Furthermore, provision is made in accordance with a preferred embodiment of the method according to the invention for the respective outer spring and the inner spring associated with the respective outer spring to be wound or formed from a single continuous material layer (for example elongated element, such as a wire, or a flat planar element, see above), wherein the two interconnected distal ends of the respective outer spring and of the inner spring associated with the respective outer spring are interconnected in one piece and are formed by a middle region of the respective material layer.

Furthermore, provision is made in accordance with a preferred embodiment for a multiplicity of through-openings (in particular in the form of parallel slots) to be formed in the respective material layer (in particular in the case of planar elements) in order to selectively influence the elasticity properties of the respective material layer or the springs formed therefrom.

Figure 1:
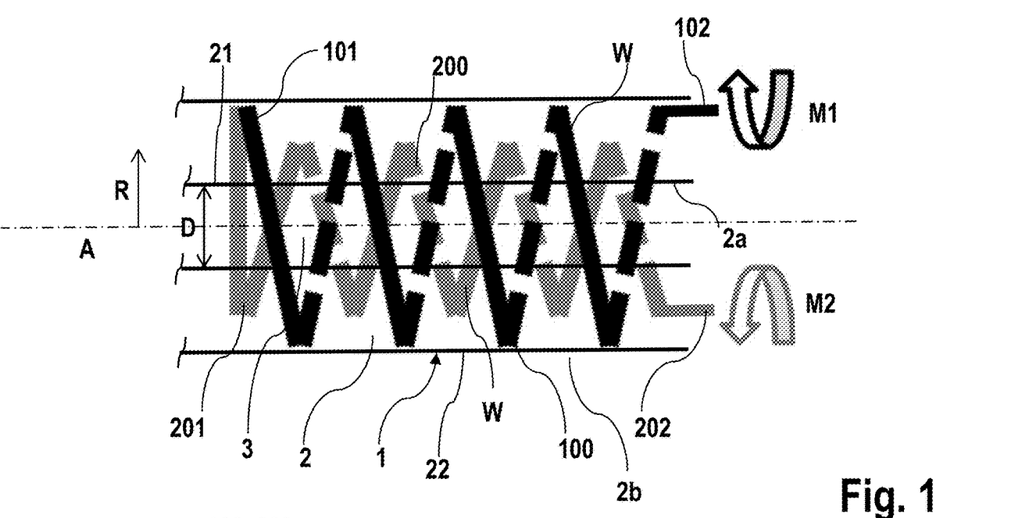
FIG. 1 shows a schematic sectional view of a catheter according to the invention with variable diameter.

FIG. 1 shows a catheter 1 according to the invention. This has a cylindrical wall 2 extended in an axial direction A and surrounding a lumen 3 of the catheter 1, which lumen is extended in the axial direction A, the catheter having an adjustable diameter D perpendicularly to the axial direction A, that is to say in the radial direction R.

For this purpose, provision is made in accordance with the invention for the wall 2 to have at least one outer spring 100 and at least one inner spring 200, which is arranged coaxially to the outer spring (with respect to the central axis A or the axial direction A), wherein the at least one outer spring 100 surrounds the at least one inner spring 200.

The wall 2 can also have an elastic inner material layer 21 facing toward the lumen 3, the material layer being composed in particular of a polymer and forming an inner side 2a of the wall 2 facing toward the lumen 3. The wall 2 can also have an elastic outer material layer 22, in particular composed of a polymer, which forms an outer side 2b of the wall 2 facing away from the lumen 3, wherein the inner and outer springs 100, 200 are arranged between the two material layers 21, 22 and are therefore embedded in the wall 2. In principle, however, the springs 100, 200 in all embodiments can also be embedded or arranged in the wall in a different way.

The two springs 100, 200 also each have a distal end 101, 201, which are fixedly interconnected, preferably in one piece. The two springs 100, 200 also each have a multiplicity of windings W, wherein the winding direction of the outer spring 100 is opposite the winding direction of the inner spring 200.

If a torque M1 or M2 is now exerted onto the proximal ends 102, 202 of the two spring ends 100, 200 respectively, wherein the two torque vectors are opposite one another and for example are of identical magnitude (for example parallel to the central axis A and antiparallel to the central axis A), the diameter of the individual windings W and therefore the diameter of the lumen 3 enlarges or reduces depending on the direction of the torques M1, M2, as can be seen on the basis of FIG. 1.

Figure 2:
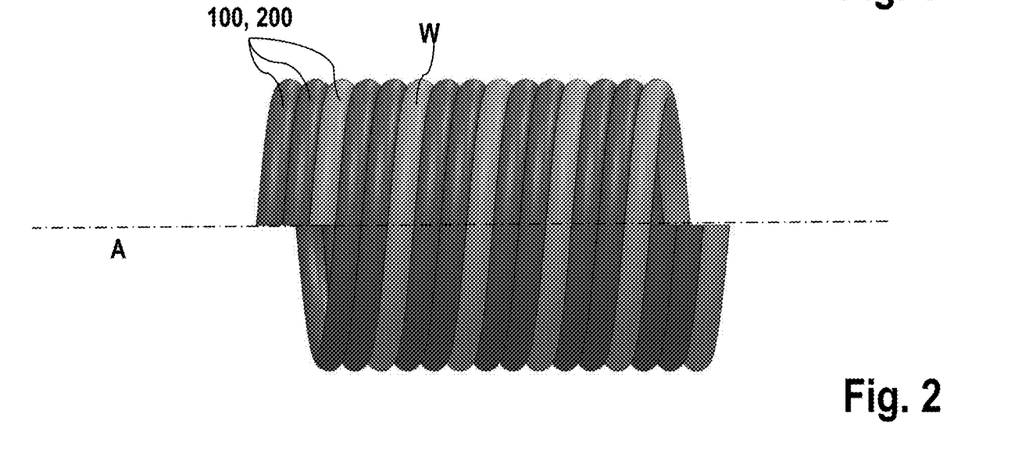
FIG. 2 shows a side view of three coil springs, which are arranged relative to one another so that they form a multi-thread (here a triple-thread) tension spring, which for example can be used as an outer spring of a catheter according to the invention.
Figure 3:
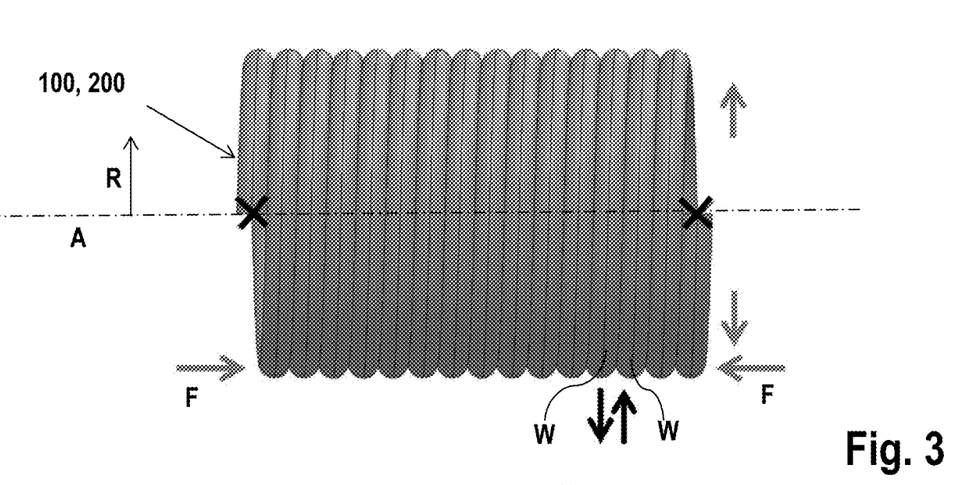
FIG. 3 shows a side view of a tension spring in order to illustrate the characteristics of the tension spring.

According to FIG. 2 the outer and/or the inner springs 100, 200 can each be formed as a coil spring, wherein coil springs of this type are preferably arranged inside one another such that an accordingly multi-thread tension spring is formed, as illustrated in FIG. 2 (here triple-thread, since three coil springs are arranged inside one another accordingly). Here, the individual windings W of the springs 100 and 200 bear against one another in the axial direction A. As shown in FIG. 3, a tension spring 100, 200 of this type can advantageously absorb high forces F in the axial direction A, since adjacent windings W bear against one another in the axial direction A and support one another mutually. Due to the arrangement of the windings W, however, these can slide relative to one another in the radial direction R.

Figure 4:
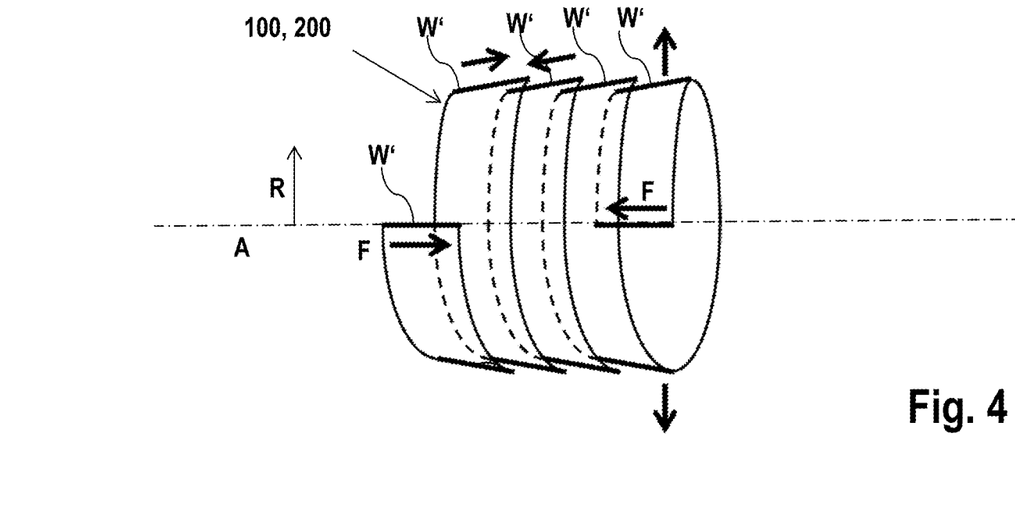
FIG. 4 shows a schematic view of a helical spring in order to illustrate the characteristics of the helical spring.
Figure 8:
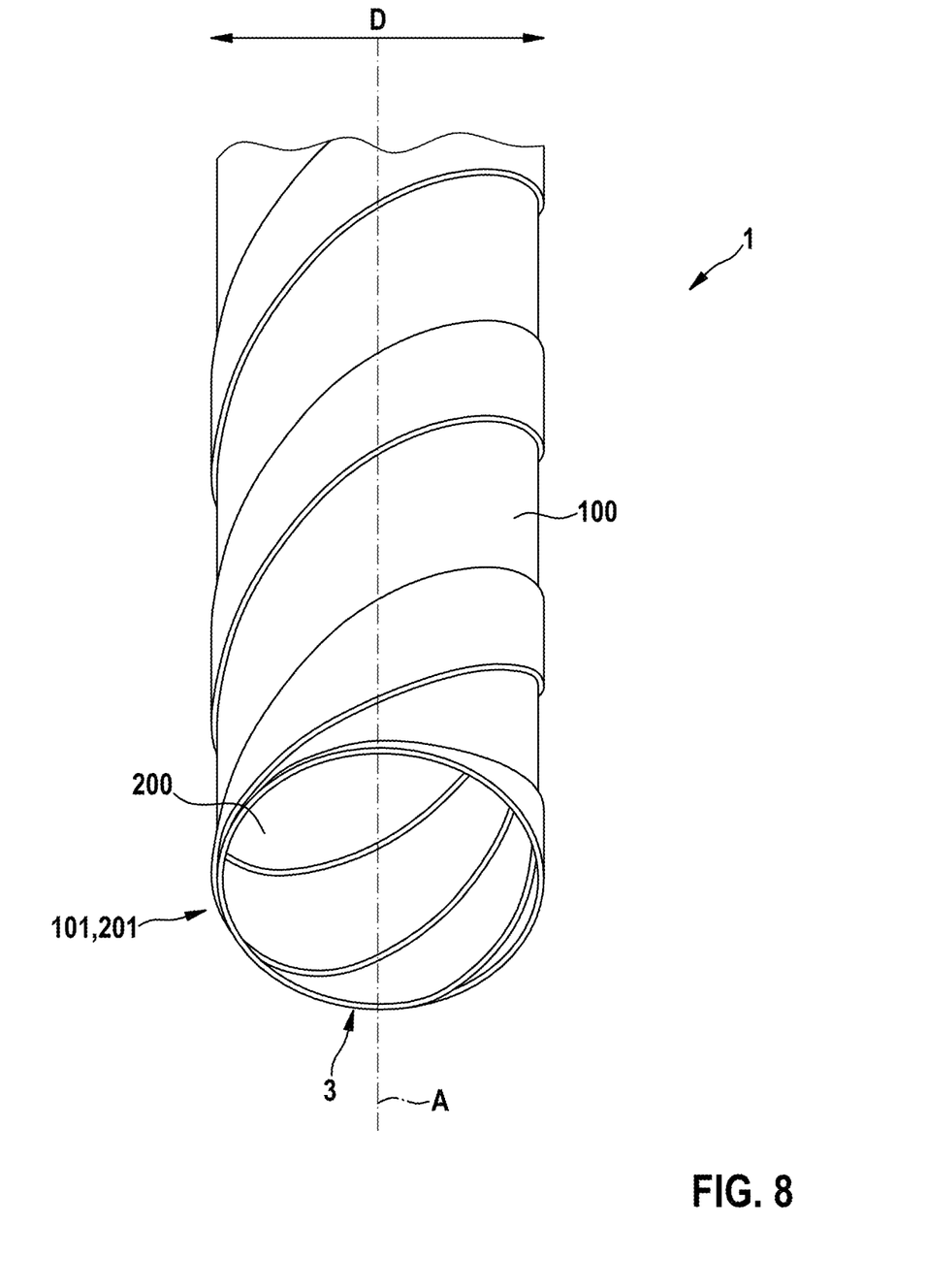
FIG. 8 shows a detailed illustration of a spring structure of a catheter according to the invention having a multi-thread inner helical spring and a multi-thread outer helical spring.

Alternatively, the inner and the outer springs 100, 200 can also each be formed as a helical spring 100, 200, as is shown in FIG. 4. A helical spring 100, 200 of this type is characterised by a multiplicity of windings W' which are flat in cross-section, wherein adjacent windings W' overlap one another in the radial and axial direction R. Here, the axial direction A or the central axis A of the helical spring 100 or 200 lies in the cross-sectional plane with respect to which the cross-sections of the winding W' are formed flat, which is indicated in FIG. 4 by bold lines. As can be inferred from FIG. 4, helical springs 100, 200 of this type have the property that the individual windings W' advantageously cannot slide relative to one another in the radial direction R, as is the case with the tension springs 100 and 200 according to FIGS. 2 and 3 respectively. For this reason, helical springs 100 and 200 of this type can only absorb low forces in the axial direction A—with regard to an individual structure— since the windings W' overlap and the helical spring 100 or 200 according to FIG. 4 can be compressed in the axial direction A. For the case however that both an inner and outer structure are present (whether composed of one or more elements in each case), the spring structure according to the invention is capable of absorbing axial forces. If, specifically, the inner structure compresses, the diameter slightly increases at the same time because the overlap also increases. The outer structure, since it in particular is wound precisely in the reverse manner, experiences a reduction of the diameter when it is compressed. The two structures support one another mutually in the radial direction, such that a compression in the axial direction is hindered. A structure as shown in FIG. 8 can therefore also absorb axial forces.

In accordance with a further embodiment provision is made for tension springs and helical springs of the type according to FIGS. 2, 3 and 4 to be combined with one another. A catheter 1 having a spring structure of this type is shown in detail in FIG. 5. This spring structure has five outer springs 100 in the form of coil springs, which are arranged such that a five-thread tension spring is formed, which extends in the axial direction A, wherein the individual windings W of the tension spring are wound helically around the axial direction A or central axis A. Here, adjacent windings W bear against one another in the axial direction A. The five outer springs 100 also surround five inner springs 200, which are each formed as helical springs 200, wherein these helical springs 200 are arranged relative to one another such that they extend coaxially to the outer springs 100 and form a five-thread helical (inner) spring, of which adjacent windings W' overlap one another in the radial and axial direction R.

The distal ends 101 of the outer springs 100 are each secured to an associated distal end 201 of a helical spring 200. The torques M1 and M2 can then be applied via the proximal ends 102, 202 (not shown here) in order to adjust, in particular to enlarge, the diameter D. The outer diameter of the arrangement shown in FIG. 5 can be enlarged here, for example, by 6 mm to 9 mm. The wall thickness of the shown spring arrangement is for example approximately 325 µm. The length of the shown spring structure is for example approximately 35 mm with 6 mm outer diameter and approximately 23 mm with 9 mm outer diameter.

Figure 6:
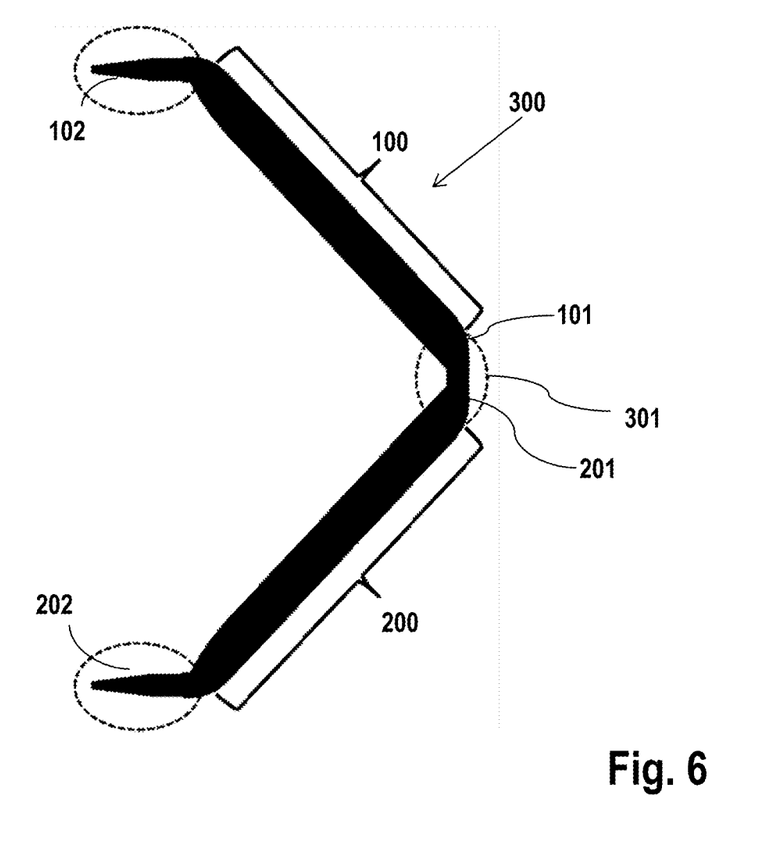
FIG. 6 shows a plan view of a material layer used for the production of an inner helical spring integrally connected to an outer helical spring.

For the case in which the outer and the inner springs 100, 200 are formed as helical springs (for example of the type according to FIG. 4), each outer helical spring 100 can be formed integrally with an associated inner helical spring 200 from a flat material layer 300 or a flat planar element 300, which for example can be cut out from a flat metal plate by means of a laser. A planar element 300 of this type is shown in FIG. 6. The material layer 300 here has a first flat limb 100 for forming the outer spring 100 and a second flat limb 200 connected in one piece to the first limb 100, the second limb serving to form the inner spring 200. Here, the first limb 100 is connected via a middle portion 301 of the material region 300 to the second portion 200 in an integral or one-piece manner. In order to produce the two springs 100, 200, the second limb 200 is now wound around the direction of extension of the proximal end 202 (downwardly in FIG. 6), wherein a helical inner spring 200 having overlapping windings W' of the type according to FIG. 4 is produced (in particular for the case in which the inner or outer structure consists of just one helical spring). The first limb 100, for production of the outer spring 100, is then wound in the opposite direction around the extension direction of the proximal end 102 (upwardly in FIG. 6). The two springs 100, 200 can also be produced in the reverse order (firstly the first limb 100 and then the second limb 200). Here, two distal ends 101, 201 of the two springs 100, 200 are produced, which are already connected to one another in one piece. The relevant torque M1 or M2 can then be introduced into the two proximal ends 102, 202, which in the starting state according to FIG. 6 are oriented parallel to one another.

Figure 7:
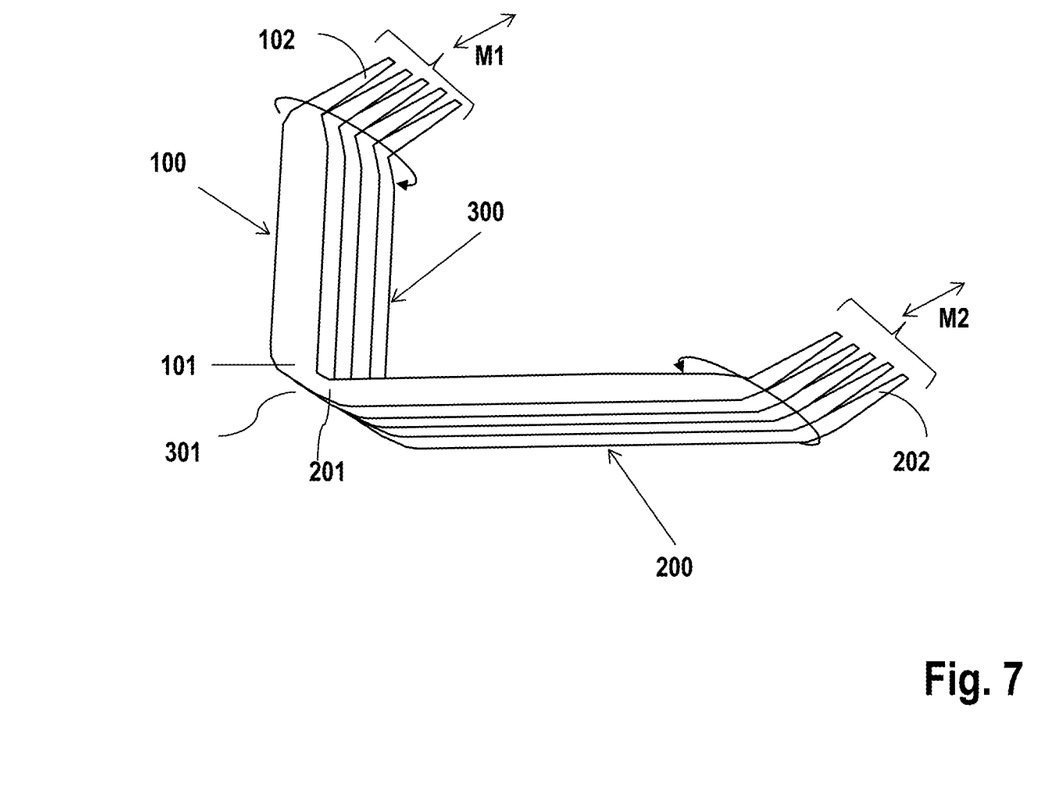
FIG. 7 shows a schematic view of a plurality of material layers arranged on top of one another, which are arranged offset from one another and can be rolled up to form a spring structure having a multi-thread inner helical spring and a multi-thread outer helical spring.

In accordance with the principle shown in FIG. 6, a plurality of material layers 300 or planar elements 300 arranged above one another and offset relative to one another can, of course, also be processed to form a plurality of continuous outer and inner springs 100, 200. FIG. 7 shows, for such a situation, the basic relative arrangement of the material layers 300 relative to one another, which are each produced separately (see also above). The five proximal ends 202 of the inner limbs 200 are then interconnected and fixedly held. The material layers 300 are secured in the middle region 301 and a certain torque is applied there until the inner limbs 200 overlap and an inner structure is thus formed. The proximal ends 102 of the outer limbs 100 are then interconnected. An opposite torque is applied there until the outer limbs 100 overlap and an outer structure is thus formed. The middle region 301 is then released again.

A spring structure of a catheter 1 according to the invention produced in this way is shown by way of example in FIG. 8.

Here as well the outer diameter of the shown spring structure can be enlarged for example by 6 mm to 9 mm. The wall thickness of the shown spring structure is, for example, 250 µm. The spring structure has an approximate length of, for example, 37 mm, which changes with the outer diameter of the shown spring structure.

Figure 5:
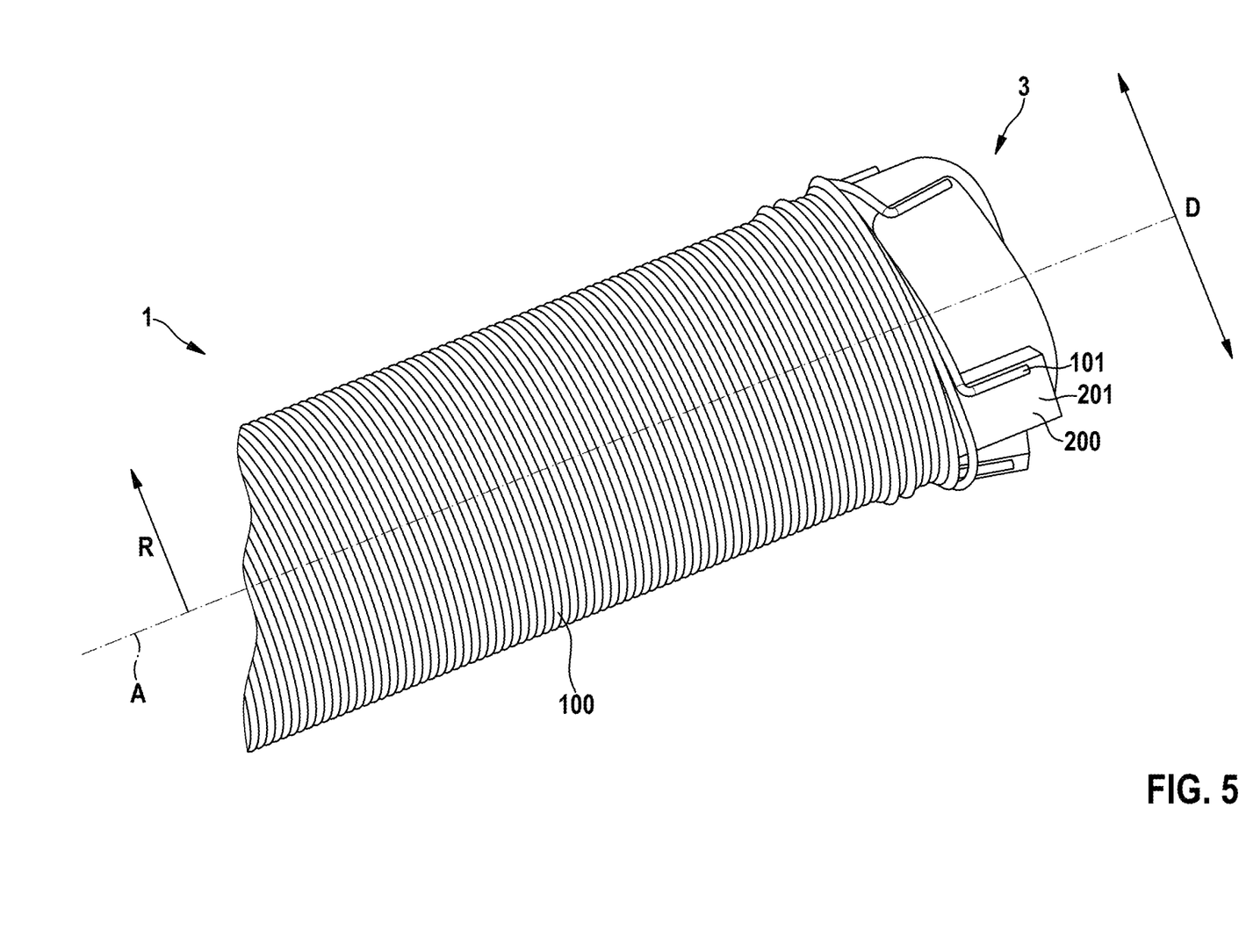
FIG. 5 shows a detailed illustration of a spring structure of a catheter according to the invention, wherein the outer springs are formed by tension springs and the inner springs are formed by helical springs.

If more then two proximal ends 102, 202 are provided, for example as in the embodiments in FIGS. 5 and 8, the proximal ends 202 of the inner springs 200 are interconnected. The proximal ends 102 of the outer springs 100 can be interconnected in the same way. The proximal ends 202 and 102 combined in this way can then be moved relative to one another in order to adjust the diameter D using a suitable means by exerting suitable, oppositely directed torques (M1, M2) onto the combined proximal ends 102 and 202.

Figure 10:
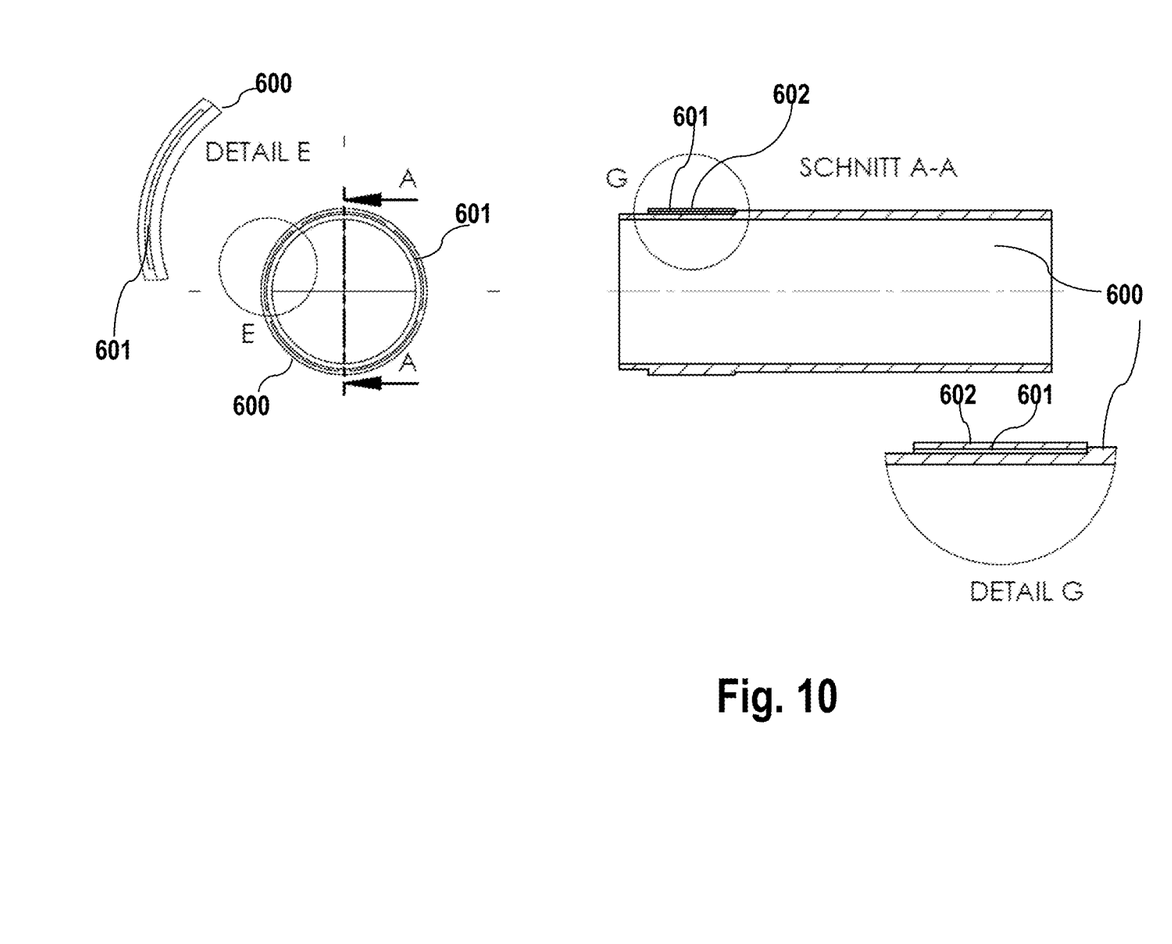
Figure 11:
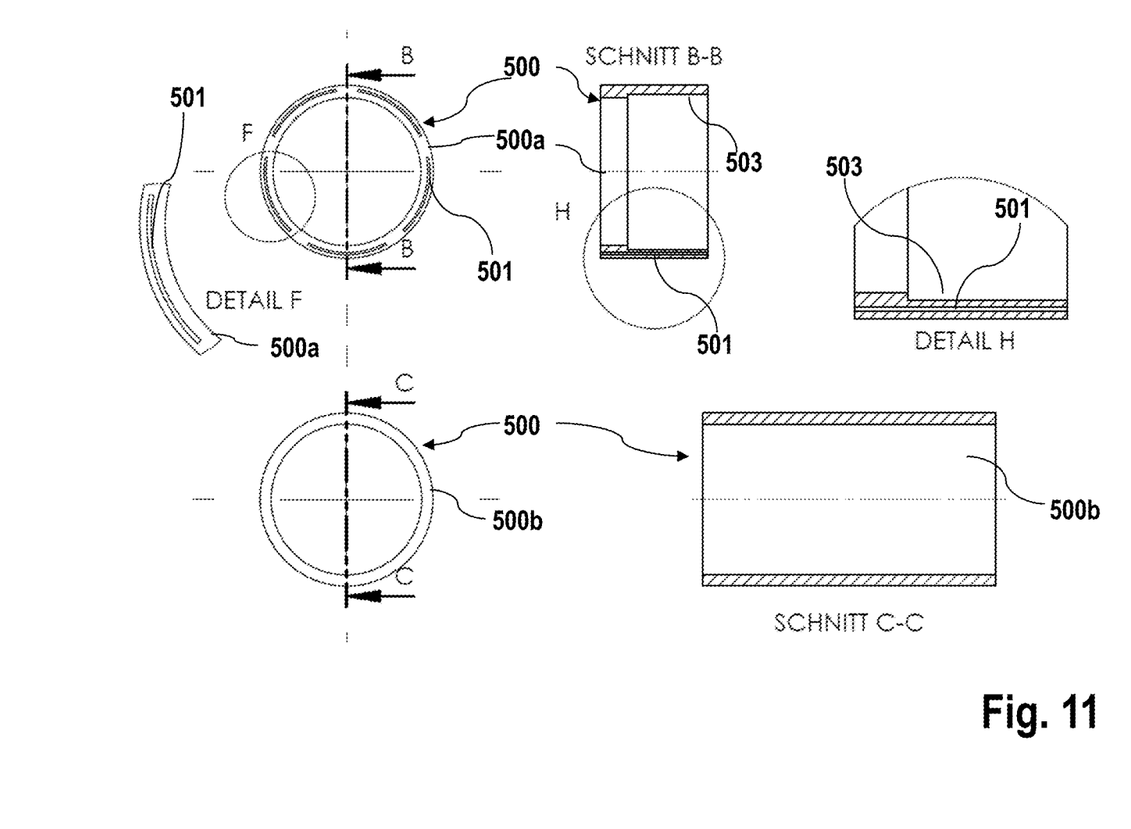
Figure 12:
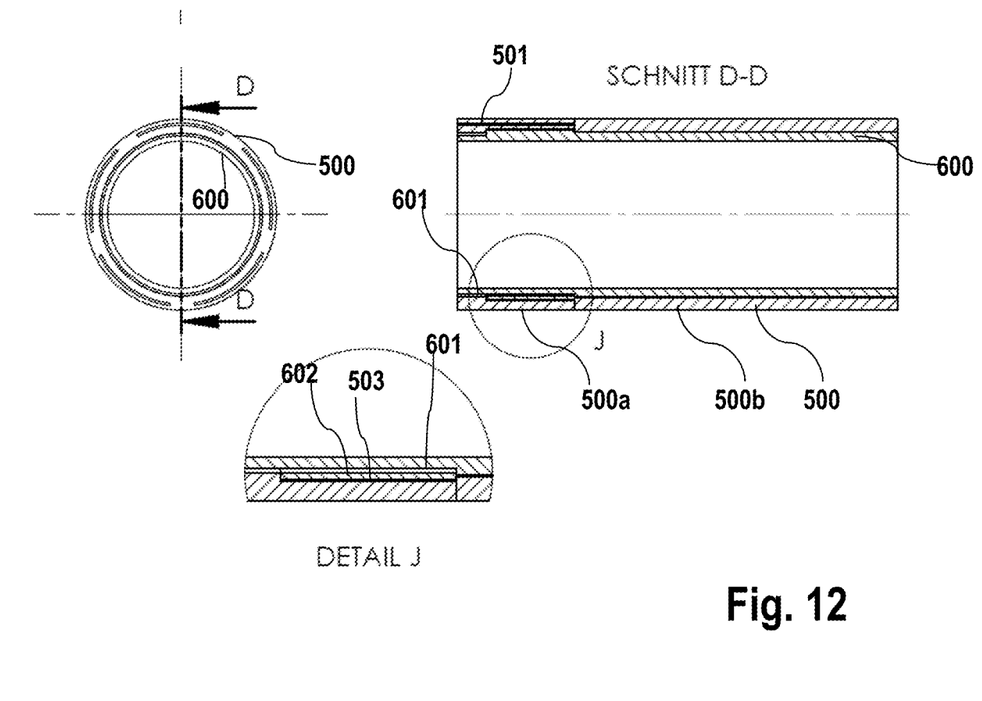
-FIG. 12 shows schematic sectional views of an inner and outer holder for introducing torques into the proximal ends of the springs.

FIGS. 10 to 12 showed a possible embodiment of a means for exerting torques onto the proximal ends 102, 202 of the springs 100, 200, wherein this means is formed here in the manner of an inner holder and an outer holder 600, 500, the outer holder being coaxial to the inner holder and the holders being rotatable relative to one another so that the torques can be exerted on the proximal ends 102 of the outer springs 100 on the one hand and on the proximal ends 202 of the inner springs 200 on the other hand. The holders 500, 600, which are cylindrical here, can each be fixed for example to an associated catheter so that the two holders 500, 600 can be rotated relative to one another via the catheter (which is likewise coaxial).

In order to receive and fix the proximal ends 202 of the inner springs 200, the inner holder 600 has slots 601 in the end face, wherein the inner holder 600 also forms a peripheral protrusion 602, which engages in a corresponding recess 503 in the cylindrical outer holder 500 so that the two holders 500, 600 cannot be moved axially relative to one another, but can only be rotated relative to one another about the axial direction.

Furthermore, the outer holder 500 for the proximal ends 102 of the outer springs 100 also has end-face slots 501, in which the proximal ends 102 of the outer springs 100 can be fixed.

So that the inner holder 600 can be arranged with its protrusion 602 in the recess 503 in the outer holder 500, the outer holder 500 can initially be embodied in two parts and can have two portions 500*a*, 500*b* accordingly, wherein a first portion 500*a*, which comprises the slots 501 and the recess 503, is initially positioned on the inner holder 600 so that this engages in the recess 503 via the protrusion 602. The second portion 500*b* can then be arranged in abutment on the first portion 500*a* and can be connected thereto, in particular welded thereto (for example by laser welding).

If the outer holder 500 is now rotated relative to the inner holder 600, the above-described torques M1 and M2 can be introduced into the proximal ends 102, 202 of the springs 100, 200.

Figure 9:
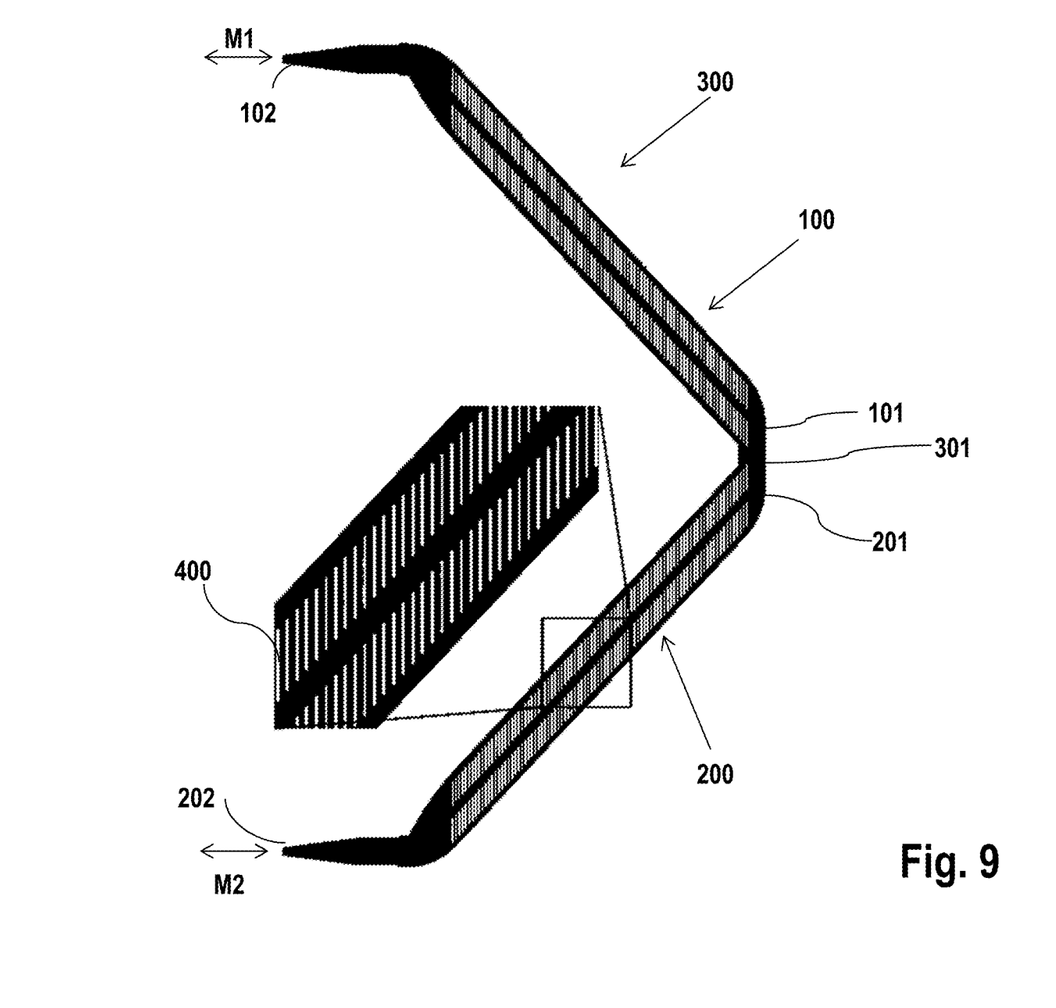
FIG. 9 shows a plan view of a material layer of the type according to FIG. 6, wherein here the material layer has a multiplicity of parallel through-openings for influencing the elasticity properties of the material layer; and FIG. 10

FIG. 9 shows, lastly, the possibility of providing the individual material layers 300 with through-openings 400. Here, the through-openings may be, for example, a multiplicity of slots formed parallel to one another, which for example can be formed perpendicularly to the winding direction of the limbs 100 and 200. By means of through-openings 400 of this type in the respective material layer 300 or in the respective planar element 300, the elasticity properties of the springs 100 and 200 to be produced can be selectively influenced and controlled.

As a result, the spring structure according to the invention is advantageously able to generate a certain radial force with each adjusted diameter D of the lumen 3. The catheter 1 according to the invention, at each adjusted diameter D, can thus withstand a significant internal pressure in the lumen (for example caused by a compressed stent or a compressed heart valve prosthesis). Furthermore, the catheter 1 according to the invention, on account of the aforementioned property, is able to compress a heart valve prosthesis starting from a large diameter to a smaller diameter. This is advantageous in particular for what is known as re-sheathing, in which case the heart valve prosthesis is to be received again in the catheter. For example, by means of the present invention, the heart valve prosthesis can thus be received with the enlarged diameter of the catheter, wherein the diameter of the catheter is only then reduced by means of the mechanism according to the invention. Strong axial forces on the heart valve can be avoided as a result, which otherwise would be produced when the prosthesis is withdrawn into a catheter that is relatively small in the radial direction. Furthermore, the spring structure according to the invention is also able to absorb a certain axial force at each adjusted diameter.

The invention claimed is:

1. A catheter having an adjustable diameter, the catheter comprising:
a wall extending in an axial direction surrounding a lumen of the catheter, the wall having at least one outer spring and at least one inner spring arranged coaxially to the at least one outer spring, wherein the at least one outer spring surrounds the at least one inner spring, wherein the at least one inner and outer springs each have a distal end which are connected to one another, and wherein the at least one inner and outer springs each have a plurality of windings, wherein a winding direction of the at least one outer spring is opposite to a winding direction of the at least one inner spring and wherein the at least one inner and outer springs each have a proximal end opposite their respective distal ends, and are configured such that the diameter can be adjusted by application of a first torque to the proximal end of the at least one outer spring and by application of a second torque to the proximal end of the at least one inner spring, wherein the first torque is opposite the second torque.

2. The catheter as claimed in claim 1, wherein the at least one outer spring comprises a coil tension spring, in which adjacent windings bear against one another in the axial direction.

3. The catheter as claimed in claim 1, wherein the at least one outer spring comprises a helical spring, wherein the plurality of windings are flat in cross-section, and wherein adjacent windings of the helical spring overlap one another in a radial direction and the axial direction.

4. The catheter as claimed in claim 1, wherein the at least one inner spring comprises a coil tension spring, in which adjacent windings bear against one another in the axial direction.

5. The catheter as claimed in claim 1, wherein the at least one inner spring comprises a helical spring wherein the plurality of windings are flat in cross-section, and wherein adjacent windings of the helical spring overlap one another in a radial direction and the axial direction.

6. The catheter as claimed in claim 1, wherein the at least one inner spring and the at least one outer spring are formed together from a single continuous material layer, wherein the two interconnected distal ends are interconnected in one piece and are formed by a middle portion of the material layer.

7. The catheter as claimed in claim 1, comprising a plurality of outer springs and corresponding plurality of inner springs arranged coaxially to the plurality of outer springs, wherein each of the plurality of the outer springs surrounds and is connected to a distal end of an associated one of the plurality of inner springs.

8. The catheter as claimed in claim 7, wherein each of the plurality of inner and outer springs comprises a proximal end opposite a respective distal end, and wherein the diameter can be adjusted by application of the first torque to the proximal ends of the plurality of outer springs and the second torque to the proximal ends of the plurality of inner springs.

9. The catheter as claimed in claim 7, wherein each of the plurality of outer springs comprises a multi-thread outer coil tension spring, in which adjacent windings bear against one another in the axial direction.

10. The catheter as claimed in claim 7, wherein each of the plurality of outer springs comprises a helical spring having a multiplicity of windings which are flat in cross-section, wherein the helical springs each form a multi-thread outer helical spring, wherein adjacent windings of each of the outer helical springs overlap one another in a radial direction and the axial direction.

11. The catheter as claimed in claim 7, wherein each of the plurality of inner springs comprises a multi-thread inner coil tension spring, in which adjacent windings bear against one another in the axial direction.

12. The catheter as claimed in claim 7, wherein each of the plurality of inner springs comprises a helical spring having a multiplicity of windings which are flat in cross-section, wherein the helical springs each form a multi-thread inner helical spring, wherein adjacent windings of the inner helical springs overlap one another in a radial direction and the axial direction.

13. The catheter as claimed in claim 7, wherein respective ones of the plurality of outer springs and inner springs are each formed from a single continuous material layer, wherein the respective ones of the outer springs and inner springs are interconnected in one piece and are formed by a middle portion of the respective material layer.

14. The catheter as claimed in claim 13, wherein the respective material layer comprises a plurality of through-openings.

15. The catheter as claimed in claim 1, wherein the wall comprises an elastic inner material layer facing toward the lumen, which material layer is composed of a polymer and forms an inner side of the wall facing toward the lumen, and the wall comprises an elastic outer material layer, composed of a polymer, which forms an outer side of the wall facing away from the lumen, and wherein the at least one inner and outer springs are arranged between the inner and outer material layers.

* * * * *